United States Patent
Smith et al.

(10) Patent No.: US 10,682,087 B2
(45) Date of Patent: Jun. 16, 2020

(54) APPARATUS, METHOD, AND SYSTEM FOR TESTING HUMAN OLFACTORY SYSTEMS

(71) Applicant: Olfaxis, LLC, Durham, NC (US)

(72) Inventors: David W. Smith, Durham, NC (US); Jesse S. Eberdt, III, Durham, NC (US)

(73) Assignee: Olfaxis, LLC, Durham, NC (US)

( * ) Notice: Subject to any disclaimer, the term of this patent is extended or adjusted under 35 U.S.C. 154(b) by 642 days.

(21) Appl. No.: 15/087,181

(22) Filed: Mar. 31, 2016

(65) Prior Publication Data

US 2016/0287161 A1  Oct. 6, 2016

Related U.S. Application Data

(60) Provisional application No. 62/142,726, filed on Apr. 3, 2015.

(51) Int. Cl.
*A61B 5/00* (2006.01)

(52) U.S. Cl.
CPC .......... *A61B 5/4088* (2013.01); *A61B 5/4011* (2013.01)

(58) Field of Classification Search
CPC .................................................. A61B 5/4011
See application file for complete search history.

(56) References Cited

U.S. PATENT DOCUMENTS

| | | | |
|---|---|---|---|
| 5,325,765 A | 7/1994 | Sylvan et al. | |
| 5,840,189 A | 11/1998 | Sylvan et al. | |
| 6,059,724 A | 5/2000 | Campell et al. | |
| 6,325,475 B1 * | 12/2001 | Hayes | A61B 5/00 128/203.11 |
| 6,338,715 B1 | 1/2002 | Hayes et al. | |
| 6,557,394 B2 | 5/2003 | Doty | |
| 6,589,577 B2 | 7/2003 | Lazaris et al. | |
| 6,607,762 B2 | 8/2003 | Lazaris et al. | |
| 6,645,537 B2 | 11/2003 | Sweeney et al. | |
| 6,658,989 B2 | 12/2003 | Sweeney et al. | |
| 8,429,950 B2 | 4/2013 | Wright | |
| 8,469,293 B2 | 6/2013 | Doty et al. | |
| 8,820,265 B2 | 9/2014 | Palmer et al. | |

(Continued)

FOREIGN PATENT DOCUMENTS

| | | |
|---|---|---|
| EP | 2174585 | 4/2010 |
| WO | 2006135368 | 12/2006 |

(Continued)

OTHER PUBLICATIONS

Alaoui-Ismaïli et al (Odor hedonics: connection with emotional response estimated by autonomic parameters, 1997, Chem Senses, 22(3): 237-48).*

(Continued)

*Primary Examiner* — Kaylee R Wilson
*Assistant Examiner* — Jay B Shah
(74) *Attorney, Agent, or Firm* — Myers Bigel, P.A.

(57) ABSTRACT

An apparatus, module, methods and systems for automated, standardized assessment and analysis of a human olfactory system's odor detection ability as an indicator or predictor of cognitive impairment or change in cognitive health, and other health conditions such as diabetes. Notably, the present invention is operable for use across all age groups of humans and provides quantitative detection and analysis of a human olfactory system's detection ability compared to a relevant demographic population.

19 Claims, 11 Drawing Sheets

(56) References Cited

U.S. PATENT DOCUMENTS

| | | | |
|---|---|---|---|
| 2006/0261179 A1* | 11/2006 | Davies | A01M 1/2044 239/34 |
| 2007/0077204 A1 | 4/2007 | Devanand et al. | |
| 2007/0186923 A1* | 8/2007 | Poutiatine | A61J 7/0038 128/200.14 |
| 2007/0295327 A1 | 12/2007 | Bottomley | |
| 2013/0156897 A1 | 6/2013 | Goldstein | |
| 2013/0270176 A1 | 10/2013 | Scheiber | |
| 2014/0221269 A1 | 8/2014 | Sobel et al. | |
| 2015/0112161 A1 | 4/2015 | Mills | |
| 2016/0015309 A1 | 1/2016 | Mills | |
| 2016/0287161 A1 | 10/2016 | Smith et al. | |
| 2018/0110457 A1* | 4/2018 | Smith | A61B 5/4011 |

FOREIGN PATENT DOCUMENTS

| | | |
|---|---|---|
| WO | 2010100567 | 4/2010 |
| WO | 2014154909 | 10/2014 |

OTHER PUBLICATIONS

Ottaviano et al (N-butanol olfactory threshold and nasal patency before and after palatal expansion in children. A preliminary study, 2014, Int J Pediatr Otorhinolaryngol, 78(10): 1618-23).*

Bodyak N and Slotnick B, 1999. Performance of Mice in an Automated Olfactometer: Odor Detection, Discrimination and Odor Memory. 24 (6): 637-645.

Lundstrom et al. "Methods for building an inexpensive computer-controlled olfactometer for temporally precise experiments" International Journal of Psychophysiology, 78(2):179-189 (2010).

Ramalho et al. "Evolution of the perceived odour intensity assessed by GC-Olfactometry of emissions from household and building products" Poster presentation, CSTB Healthy Buildings 2006.

Alosco et al. "Olfactory Function and Associated Clinical Correlates in Former National Football League Players" Journal of Neurotrauma, 34:772-780 (2017).

Bakker et al. "Olfactory Dysfunction in Pediatric Traumatic Brain Injury: A Systematic Review" Journal of Neurotrauma, 31:308-314 (2014).

Bakker et al. "Recovery of Olfactory Function following Pediatric Traumatic Brain injury: A Longitudinal Follow-Up" Journal of Neurotrauma, 33:777-783 (2016).

Cain et al. "Uniformity of Olfactory Loss in Aging" Annals of the New York Academy of Sciences, 561:29-38 (1989).

Callahan et al. "Assessment of Anosmia After Traumatic Brain injury: Performance Characteristics of the University of Pennsylvania Smell Identification Test" Journal of Head Trauma Rehabilitation, 17(3) 251-256 (2002).

Caminiti et al. "Detection of Olfactory Dysfunction Using Olfactory Event Related Potentials in Young Patients with Multiple Sclerosis" PLoS ONE, 9(7):e103151 (2014).

Coelho et al. "Posttraumatic olfactory dysfunction" Auris Nasus Larynx, 43:137-143 (2016).

De Guise et al. "Olfactory and executive dysfunctions following orbito-based lesions in traumatic brain injury" Brain Injury, 29(6):730-738 (2015).

Dhilla Albers et al. "Episodic Memory of Odors Stratifies Alzheimer Biomarkers in Normal Elderly" Annals of Neurology, 80(6):846-857 (2016).

Doty et al. "A Study of the Test-retest Reliability of Ten Olfactory Tests" Chemical Senses, 20:645-656 (1995).

Drummond et al. "The Invisible Problem: The Incidence of Olfactory Impairment following Traumatic Brain injury" Brain Impairment, 16(3): 196-204 (2015).

Gudziol et al. "The impact and prospect of traumatic brain injury on olfactory function: a cross-sectional and prospective study" European Archives of Oto-Rhino-Laryngology, 271: 1533-1540 (2014).

Hedner et al. "Cognitive factors in odor detection, odor discrimination, and odor identification tasks" Journal of Clinical and Experimental Neuropsychology, 32(10):1062-1067 (2010).

International Search Report and the Written Opinion of the International Searching Authority corresponding to International Patent Application No. PCT/US2016/025519 (10 pages) (dated Jul. 1, 2016).

Larsson et al. "Odor Identification in Old Age: Demographic, Sensory and Cognitive Correlates" Aging, Neuropsychology, and Cognition, 12(3):231-244 (2005).

Lötsch et al. "How Many and Which Odor Identification Items Are Needed to Establish Normal Olfactory Function?" Chemical Senses, 41:339-344 (2016).

Osborne-Crowley et al. "Hyposmia, Not Emotion Perception, Is Associated With Psychosocial Outcome After Severe Traumatic Brain Injury" Neuropsychology, 30(7):820-829 (2016).

Ruff et al. "A Quantative Test for Olfaction Is the Most Sensitive Physical Examination Biomarker for Residual Neurological Dysfunction Due to Mild Traumatic Brain Injury (mTBI) That Can Be Performed in the Setting of a Clinical Examination Room (P04. 022)" Neurology, 80(7 Supplement) (5 pages) (2013).

Schofield et al. "Traumatic brain injury and olfaction: a systematic review" Frontiers in Neurology, 5(5):1-22 (2014).

Sigurdardottir et al. "Olfactory Identification and Its Relationship to Executive Functions, Memory, and Disability One Year After Severe Traumatic Brain Injury" Neuropsychology, 30(1):98-108 (2016).

Tabert et al. "A 10-Item Smell Identification Scale Related to Risk for Alzheimer's Disease" Annals of Neurology, 58:155-160 (2005).

Xydakis et al. "Olfactory impairment and traumatic brain injury in blast-injured combat troops" Neurology, 84:1559-1567 (2015).

Yoder et al. "Evidence of rapid recovery from perceptual odor adaptation using a new stimulus paradigm" Attention, Perception, & Psychophysics, 76(4):1093-1105 (2014).

Doty et al. "Presence of both odor identification and detection deficits in Alzheimer's disease" Brain Research Bulletin, 18(5):597-600 (1987) (Abstract only).

SBIR-STTR Award to Osmic Enterprises, Inc. from the Department of Health and Human Services, Contract 4R44AG051311-02 (3 pages) (Awards year: 2016).

Patel et al. "Impaired olfactory discrimination learning and decreased olfactory sensitivity in aged C57BI/6 mice" Neurobiology of Aging, 30(5):829-837 (2009).

Office Action issued for related U.S. Appl. No. 15/562,966 (14 pages) (dated Jan. 15, 2020).

* cited by examiner

Module FIG. 3

40 Years of Age

50 Years of Age

60 Years of Age

APPARATUS, METHOD, AND SYSTEM FOR TESTING HUMAN OLFACTORY SYSTEMS

CROSS REFERENCES TO RELATED APPLICATIONS

This application claims the benefit of U.S. Provisional Application No. 62/142,726, filed Apr. 3, 2015, which is incorporated herein by reference in its entirety.

BACKGROUND OF THE INVENTION

1. Field of the Invention

The present invention is generally directed to an apparatus, method, and system for testing human olfactory sensory system functions. More particularly the present invention operates to provide a method for the precise generation of specified olfactory system testing odorants, for use in making standardized testing of olfactory systems, data collection, assessment, and predictive or diagnostic results, and even more particularly for human olfactory system odor detection, odor adaptation, odor discrimination and odor identification ability to identify disease or disorder(s) and as a predictive element of cognitive impairment.

2. Description of the Prior Art

A decrease in olfactory function with age has been attributed to a variety of factors, including normal anatomical and physiological changes in aging, trauma, environment, exposure to toxins, medications, and disease. A decrease in olfactory function has also been determined to be one of the best predictors of five-year survival. Other research shows that changes associated with diseases such as diabetes affects olfactory function. Cognitive disease or disorder, namely Alzheimer's disease, Parkinson's disease, traumatic brain injury, Amyotrophic lateral sclerosis (ALS) and schizophrenia, are known to be associated with olfactory dysfunction. In particular, the ability to identify and discriminate the odors, as well as the odor threshold, can be altered in cognitive disorders. These changes often occur as early manifestation of the cognitive pathology but they are not always diagnosed on time. Early diagnosis can lead to slowing, stopping, or reversing the progression of cognitive decline.

U.S. Pat. No. 6,059,724 for system for predicting future health by inventors Campell, et al. filed Feb. 14, 1997 and issued May 9, 2000 is directed to a computer-based system for predicting future health of individuals comprising a computer comprising a processor containing a database of longitudinally-acquired biomarker values from individual members of a test population; a computer program that includes steps for selecting from said biomarkers a subset of biomarkers for discriminating between members, and using the distributions of the selected biomarkers to develop a statistical procedure that is capable of being used for classifying members of the test population, and estimating quantitatively, for each member of the test population, the probability of acquiring the specified biological condition.

U.S. Pat. No. 6,325,475 for devices for presenting airborne materials to the nose by inventors Hayes, et al. filed Apr. 21, 1997 and issued Dec. 4, 2001 is directed to an ink-jet dispenser for the micro-dispensation of airborne materials into an individual's airspace for inhalation or sniffing. The ink-jet dispenser will allow the study of temporal integration times, inter-nostril summation, backwards and forwards masking, and other olfactory phenomena.

U.S. Pat. No. 6,338,715 for digital olfactometer and method for testing olfactory thresholds by inventors Hayes, et al. filed Mar. 31, 2000 and issued Jan. 15, 2002 is directed to a more reliable and precise method of determining the olfactory threshold is provided by a digitally operated apparatus that dispenses controlled amounts of a volatile test fluid from a digital jetting device of the type used for ink jet printing. A precise number and size of micro droplets are dispensed onto a heater which vaporizes the fluid at a test location where a patient can sniff and report whether the odor is sensed. Incremental adjustments are made to determine the approximate threshold of olfactory perception of the odor. Sensors are included to verify dispensing and to coordinate dispensing with breathing.

U.S. Pat. No. 6,557,394 for smell test device by inventor Doty filed Apr. 2, 2001 and issued May 6, 2003 is directed to a test for assessing a person's sense of smell and more particularly, toward a test which is easy to use and can be evaluated by the individual taking the test.

U.S. Pat. No. 8,429,950 for field olfactometer with differential flow-based dynamic dilution by inventor Wright filed Aug. 5, 2010 and issued Apr. 30, 2013 is directed to a low-cost field olfactometer that may be used to determine when an environmental odor is present in the ambient air in an amount which is at or above a predetermined dilution ratio. The invention also encompasses a method of olfactometry and a replaceable diluent filter cartridge assembly employed in the olfactometer and olfactometry method.

U.S. Pat. No. 8,469,293 for digital odor generator by inventors Doty, et al. filed Apr. 16, 2010 and issued Jun. 25, 2013 is directed to a digital odor generator or olfactometer and, more particularly, toward a digital odor generator that can be used to administer various odors alone or in various combinations to a patient or subject. The digital odor generator of the invention can also be used to administer olfactory tests remotely over the Internet or other network and to collect the results and tabulate data over such networks.

U.S. Pat. No. 8,820,265 for high-throughput operant sensory discrimination apparatus and method by inventors Palmer and Salemme filed Dec. 6, 2005 and issued Sep. 2, 2014 is directed to apparatus and systems useful in sensory discrimination. Through the use of a multi-well sample plate, the high-throughput analysis apparatus and method allow for rapid sensory discrimination of a large number of samples.

US patent application 2007/077,204 for olfactory identification tests for cognitive diseases and disorders by inventors Devanand, et al. filed Apr. 13, 2006 and issued Apr. 5, 2007 is directed to smell tests (odor identification tests) that are shorter that UPSIT, yet has a statistical sensitivity and specificity equivalent to or better than UPSIT. The odor identification tests of the invention are based on a core set of six odorants, where the six odorants can be selected from the following group of odorants: menthol, clove, leather, strawberry, lilac, pineapple, smoke, soap, natural gas and lemon. The invention provides odor identification tests that can: (1) discriminate between subjects who are normal and who have a neuropsychiatric condition, cognitive disease or disorder, and/or (2) predict which subjects with mild cognitive disorders will develop various neuropsychiatric conditions or cognitive diseases and disorders. In one embodiment, the test and methods of the invention can provide an early prediction or diagnosis of Alzheimer's disease that is important for patients (including patients who have mild cognitive disorders, such as MCI) and clinicians to make plans for the future and to institute early treatment.

SUMMARY OF THE INVENTION

The present invention is generally directed to an apparatus, methods, and systems for providing standardized testing of human olfactory systems. More particularly, the present invention operates to provide testing, data collection, assessment, and predictive or diagnostic results for human olfactory systems and even more particularly for human olfactory system odor detection, discrimination, odor adaptation, and identification abilities to aid in identifying mental disease, health disorders, health conditions and serve as a predictive element of cognitive impairment.

The invention is further directed to a standardized olfactory population database for automated quantitative comparison and analysis of the olfactory system of a human based on standardized measures. The invention is still further directed to an automated odorant-delivery cartridge for use with automated apparatus, method and systems of the present invention. The invention is still further directed to a module for connecting a cartridge to a mobile computing device. The invention is further directed to a method for presenting standardized odorants and standardizing the collection of olfactory test data. Specifically, in one embodiment, the invention standardizes odorant concentration calibration and a delivery system, so that regardless of the location of one or more of the devices of the present invention, the devices will deliver the same, known odorant concentration(s). Advantageously, this approach allows for repeated testing of a patient, longitudinal testing, and development of a normative database and an Olfaxis Index for objectively quantifying degradations in olfactory function. Another advantage of this approach is in providing testing of a new patient and comparing their test results with a normative appropriate demographic population where all olfactory measures were collected with identical, standardized odorants. Advantageously, this is possible with one test of the new patient. In contrast, the prior art requires repeated, long term testing of the new patient to compare the new patient's results with the normative appropriate demographic population.

The present invention provides systems and methods for the quantitative examination and analysis of a person's odor detection (odor sensitivity), discrimination, odor adaptation, and odor identification abilities, wherein the system includes a device and database that communicate; wherein the device is automated and the database houses various population distributions of odor response abilities as a standard of comparison. More specifically, this system includes at least one device in wired or wireless electronic network communication with a server, wherein the server is in communication with the database of population distributions. If the server is not currently connected to the device, the device is operable to store the demographics of the patient/subject, the results of the patient/subject, and upload the results of the patient/subject upon a connection becoming available.

The system provides for devices to independently and autonomously transmit and receive data to and from the server. The server, which may be a remote server computer in network-based communication with the testing apparatus or device, compares received results to the individual patient's previous measures and/or to the population database for one or more odorants to quantify an Olfaxis Index of olfactory function. This real-time or near-real-time analysis and reporting of data enables the rapid screening and comparison of test subjects. Thus, the present invention provides for comparing a person's olfactory performance to a standard (their own longitudinal or their own baseline, and/or against an appropriate demographic). The Olfaxis Index can aid in diagnostics for a multiplicity of conditions. Significant olfactory dysfunction can put a person at risk of smoke/fire, eating spoiled food, change of diet to a more unhealthy diet (more sugar, salt and fat), be related to diabetes, be symptomatic of traumatic brain injury, myasthenia graves, ALS, and as a biomarker for AD and PD. The prior art fails to provide, teach or suggest such a system and corresponding methods.

These and other aspects of the present invention will become apparent to those skilled in the art after a reading of the following description of the preferred embodiment when considered with the drawings, as they support the claimed invention.

DETAILED DESCRIPTION

Figure 1:
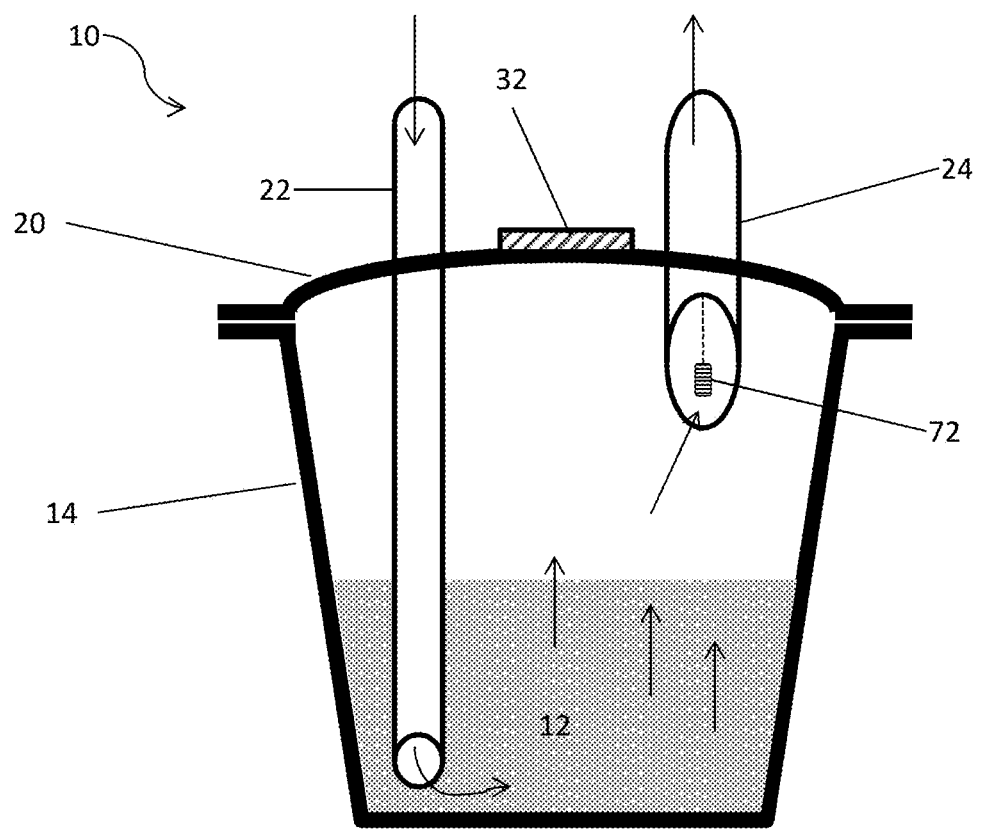
FIG. 1 illustrates a cartridge according to the present invention.

The present invention provides an apparatus, method, and system for standardized testing of human olfactory system functions. The invention includes an automated, standardized odor-delivery cartridge and odorant concentration measurement and calibration system for use with a testing apparatus having a controller for running the test sequence and capturing user input, with calibrated air flow or adapted to be connected with a smartphone or tablet computer or other computing device through a module. Preferably, the apparatus includes a photoionization detector (PID) to measure and/or calibrate the odor delivery cartridge. The apparatus is in electronic communication with at least one server computer and at least one database, preferably within a cloud-based computing network for providing real-time or near-real-time analysis of the data.

The prior art is limited regarding a standardized automated device, standardized odorants, method, or system for assessing overall olfactory functional status and predicting cognitive impairment based on odor detection, odor discrimination, odor adaptation, and odor identification. The prior art does not disclose a standardized odorant.

Thus, there is a long-standing, unmet need for a standardized, automated device, method, and system that can accurately and quantitatively examine and analyze a person's odor detection ability against their own history and against an appropriate demographic population, quantify changes in olfactory function over time, or identify dysfunction by comparing smell function against a standardized, demographic database (quantify an Olfaxis Index) in order to aid in the identification or diagnosis of physical health conditions, and to better predict a person's risk for cognitive impairment and/or other mental and related complications. The present invention solves this long-felt but unmet need by providing sealed cartridges/ampules and photoionization detectors to provide standardized concentrations of odorants.

The prior art, including U.S. Pat. No. 6,059,724 and others, fails to standardize olfactory measures. The present invention differs by standardizing olfactory measures, which allows for comparison of a new individual to the population metric (an Olfaxis Index). Standardization is essential for creation of an Olfaxis Index, and estimating quantitatively for each member of a test population, the probability of acquiring a specified biological condition (mental or physical). The present invention fulfills this long-standing unmet need by providing standardization of olfactory measures.

U.S. Pat. No. 6,338,715 describes that a precise number and size of micro droplets are dispensed onto a heater which vaporizes the fluid at a test location where a patient can sniff and report whether the odor is sensed. However, this approach is disadvantageous as the precise number and size of micro droplets assumes a chemical condition and there is no actual measure of concentration. By contrast, the present invention is advantageous in that it provides standardized concentrations. Also, the prior art reference is disadvantageous because dispensing the micro droplets onto a heater changes the molecular structure of the micro droplets, which could yield a different odor than the original unheated micro droplets.

U.S. Pat. No. 6,557,394 does not disclose measuring sensitivity of a person to an odor. Additionally, this patent document requires the test subject to (1) smell the odor and (2) identify the odor. Thus, if a person incorrectly identifies an odor or fails to identify the odor, it could be because the person can't smell the odor or the person can't identify or remember the name of the odor. Thus, this patent document requires a cognitive component, unlike the present invention which is effective at measuring smell using standardized odors. The present invention provides for measuring sensitivity of a person to an odor, which is a long-felt unmet need in the prior art.

U.S. Pat. No. 8,469,293 does not disclose standardized odorants. The generator is also costly, difficult to set up, use, and clean. In contrast, the present invention is cost effective, easy to set up, use, and clean.

US patent application 2007/077,204 does not describe measuring a sensitivity or threshold as in the present invention. Additionally, this patent document does not describe adapting to deterioration of test odorants, different temperatures, and/or humidity. There is no standardized measure disclosed by this patent document. There is also a requirement of a cognitive component to identify the odor in this prior art patent document.

Additionally, unlike the prior art, the present invention provides for measuring and standardizing olfactory functions of people of all ages for a variety of physical and mental conditions. While the present invention is operable for detecting the likelihood of a patient developing or detecting that a patient has developed Parkinson's and Alzheimer's, the present invention also provides for the detection of a variety of other disease across all age ranges. Specifically, the present invention is operable for detection of diabetes, exposures to toxins, allergies, and/or idiopathic conditions and diseases as well as predicting the onset of such conditions.

Cartridge

Figure 2:
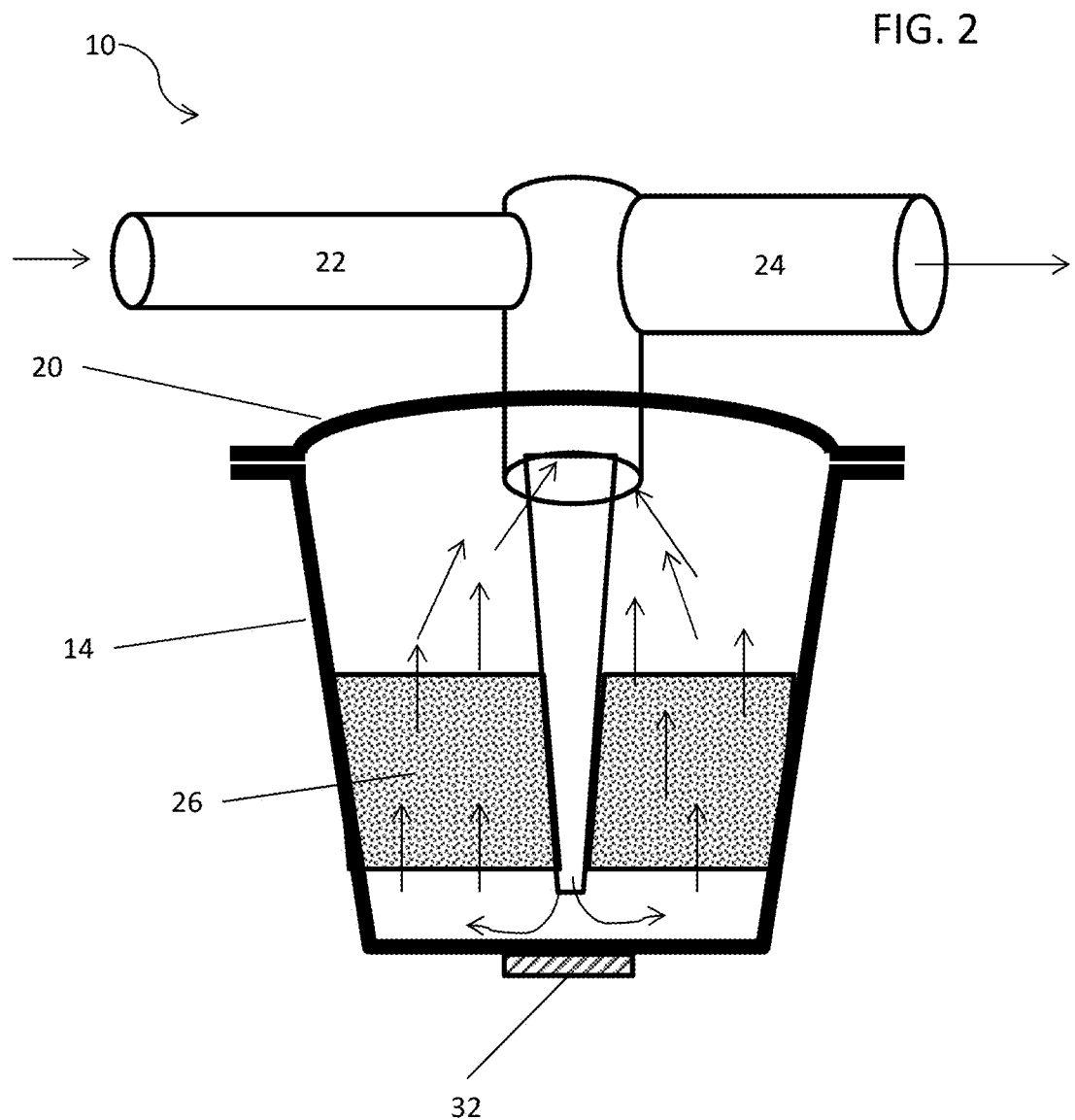
FIG. 2 illustrates another cartridge according to the present invention.

The present invention provides for a cartridge, generally described as 10 in FIGS. 1 and 2, for providing odorant for testing human olfactory systems. A cartridge is a small modular unit designed to be inserted into a larger piece of equipment. The cartridge houses, contains, or holds an odorant 12 for testing, and is connectable, by wire or wirelessly, to a computing device, which maintains control and command of the cartridge and receives input of testing results. In another embodiment, the cartridge houses, contains, or holds more than one odorant for testing, depending upon the nature of the test being run (threshold sensitivity, adaptation, odor identification, etc.). In the event that no network connection is available between the mobile computing device and the cartridge, the cartridge is operable to function independent of the mobile computing device and upload data to the mobile computing device upon restoration of a network connection between the cartridge and the mobile computing device. Thus, the communication between the cartridge and the computing device confers the delivery of the odor from the cartridge. The cartridge is smaller than odorant holders in olfactometers of the prior art and thus it is portable and disposable. The cartridge contains or holds the odorant, wherein, by way of example and not limitation, the odorant is a liquid, semi-solid, solid, or absorbed or adsorbed onto a support. The cartridge verifies that the contents match the correct stimulus paradigm by comparing the bar code on the cartridge to match the odorant and olfactometer system airflow and other operational parameters. The cartridge is also operable to verify purity for calculations of mixing to a specified percent concentration.

The cartridge 10 is preferably a sealed container constructed and configured to allow air to flow over at least one odorant 12 for creating an odor provided or presented to a human being tested. The cartridge 10 is a liquid- and odor-impermeable body and is filled with an inert gas designed to confine and preserve the odorant and the odor until the cartridge is activated. Activation of the cartridge includes any method for creating an opening into the cartridge for release of the odorant within. In a preferred embodiment, the cartridge includes an impermeable body 14 and an opening 18 that is sealingly engaged with an impermeable, pierceable cover 20 to form the liquid-impermeable, chemical-impermeable, and/or odorant-impermeable cartridge 10. The cartridge is permanently sealed with an impermeable cover, or a hermetically sealed glass ampoule to prevent odorant chemical deterioration, evaporation or oxidation to preserve odorant quality. The cartridge is preferably activated by puncturing the impermeable cover by piercing with an air inlet tube 22 and an air outlet tube 24 when the cartridge is inserted into an apparatus and activated. In an alternative embodiment, the impermeable body 14 is also pierceable. In another embodiment, the cartridge includes a glass ampoule that is broken inside a reservoir on use to ensure purity.

Preferably, the impermeable cartridge 10 holds a given volume of liquid odorant 12, the air inlet tube 22 sparges air through the odorant fluid 12, and the resulting air with odorant vapor exits the cartridge through the air outlet tube 24. In an alternative embodiment (FIG. 2), an odorant support 26 is disposed within the cartridge body to hold a solid or semi-solid odorant. The inserted air inlet and air outlet tubes are positioned relative to the odorant support in order to direct the flow of air over the odorant and prevent bypassing the odorant. In alternative embodiment, the support is a filter and the odorant is sprayed on the filter and allowed to dry. In another alternative embodiment, the support is a gel and the air inlet tube pierces through the gel, and then flows air over the surrounding gel. For creating the odorant with the ampoule, the glass ampoule is broken or dispensed into a reservoir.

The airflow tubes are separate, as shown in FIG. 1 or co-axial, as shown in FIG. 2. The co-axial tube system only requires the cover to be pierced in one location, thus reducing the risk of leakage around the tubing system.

In an alternative embodiment, the odorant and odorant support are partitioned in the cartridge body by at least one partition, wherein the partitioning allows vapor to fill the headspace of the cartridge body but restrict solid or semi-solid odorant particulate from entering the headspace, therein preventing particulate from entering the air-outlet tube. Example embodiments include U.S. Pat. Nos. 6,658,989, 6,645,537, 6,607,762, 6,589,577, 5,840,189, 5,325,765 and US Patent Publication Nos. 20130270176, 20130156897, each of which are incorporated by reference herein in their entirety.

Cartridges are designed, constructed, and configured to provide adequate headspace to meet the volumetric and/or concentration requirements of the testing to be performed, such that the necessary amount of odorant is delivered with each test. The headspace is configured and designed such that individual test actuations do not significantly diminish the headspace odor concentration. Additionally or alternatively, the apparatus is designed to control the testing actuation of a cartridge such that the headspace odor concentration is not significantly diminished. In other words, the apparatus will not actuate a test if insufficient headspace odor concentration is predetermined based on usage. In another embodiment, the test device and/or cartridge can preferably determine the absolute concentration or recognize the change in vapor pressure or volume or concentration of the odorant and correspondingly alter the airflow through the cartridge and/or alter the mixing with the carrier air so that the proper amount and concentration of the odorant is delivered. Thus, the odorant concentration in the cartridge is calibrated for each odorant delivery. In another embodiment, a separate, disposable reservoir is utilized for creating the odorant, with the cartridge preferably releasing the odorant into the reservoir.

The present invention thus provides for a cartridge for providing odorant for testing human olfactory systems. A cartridge is a small modular unit designed to be inserted into a larger piece of equipment. More particularly, the cartridge used in the present invention is designed and configured to contain an odorant and fit into a tester apparatus as described herein. The cartridge is not configured or designed for resealing after activation. In another embodiment, the cartridge is designed and configured to prevent resealing. The cartridge is a puncture-activated, non-refillable, non-resealable modular container with odorant that is standardized to provide a predetermined number of tests at a predetermined concentration and fit into a tester apparatus as described herein.

In a preferred embodiment, each cartridge also incorporates an identifier 32, such as a digital chip, bar code, etc., within, or about the cover or body to identify the odorant(s) in the cartridge. The identifier is automatically detected and read by a reader 33 and the information used to regulate the air flow and actuation rate of the cartridge. The identifier includes the odorant and/or cartridge characteristics necessary to perform the test. For example, the identifier includes the name of the odorant, carrier, concentration in carrier, headspace of the cartridge, maximum flow rate through the cartridge, maximum total odorant available, the vapor pressure, vapor ionization voltage, and any other chemical properties necessary to create a specified concentration of the odorant. The information from the identifier is communicated to the device and/or remote server to calibrate testing and standardize, normalize or otherwise correct test data for the particular odorant cartridge's properties.

In alternative embodiment, a cartridge is automated to present an odor to and obtain information from a person. Following odor presentation, the module or controller receives the user response data. The response data preferably are provided to a mobile computing device that communicates the response data with other system components.

More specifically, the cartridge houses a chip or other identifier pre-programmed to identify the odorant(s), total actuatable mass or volume of the odorant(s), and/or concentration of the odorant(s) in the headspace of the cartridge, all of which are communicated to the device. Preferably, the chip also is operable to measure a vapor pressure of the odorant. The vapor pressure is preferably used to calculate vapor concentration. The total acuatable mass or volume is the total volume, mass or amount of odor that can be delivered by test actuation from any given cartridge without affecting the concentration of the odorant and the reliability of testing. This volume or amount or concentration preferably remains constant for each cartridge type or test session. Verification of the concentration in the headspace or other concentration verification is used to indicate when the cartridge replacement is required (i.e., when the concentration is too low or the cartridge is spent). Preferably, verification of the concentration is performed via a photo ionization detector. The testing device controls and varies the delivered test air volume and test frequency. The delivered test air volume will vary based on the desired concentration to deliver to the subject and from presentation to presentation for the subject. The test frequency or trial rate (number of tests per time period) will vary based on the previous test air volume delivered, wherein the limiting factor for test frequency is the time required to saturate the headspace or otherwise ensure that the cartridge headspace has the proper odor vapor concentration, which is dictated by odorant(s) volatility and airflow.

In a preferred method, the total airflow delivered to the person being tested is constant. At the initial activation of a cartridge, the odor concentration is determined and the appropriate amount of airflow is calculated to provide adequate odor concentration for all programmed tests, e.g., for a given test session or patient or until the concentration is too low to continue (and then a new cartridge is used to replace the spent cartridge). Thereupon, for all tests the carrier airflow is adjusted to ensure constant delivered airflow and/or constant concentration while providing the appropriate odor concentration for the test. Delivered airflow is adjusted if the concentration or volume of odorant deteriorates.

The number of tests delivered per cartridge is not constant, but rather is determined by the odorant(s) physical properties and quantity and the desired delivered test air volumes.

In an alternative embodiment, the odorant is incorporated into a polymer (or other medium or containment vessel that will release odorant) that vaporizes the odorant when electrically-stimulated.

Module

Figure 3:
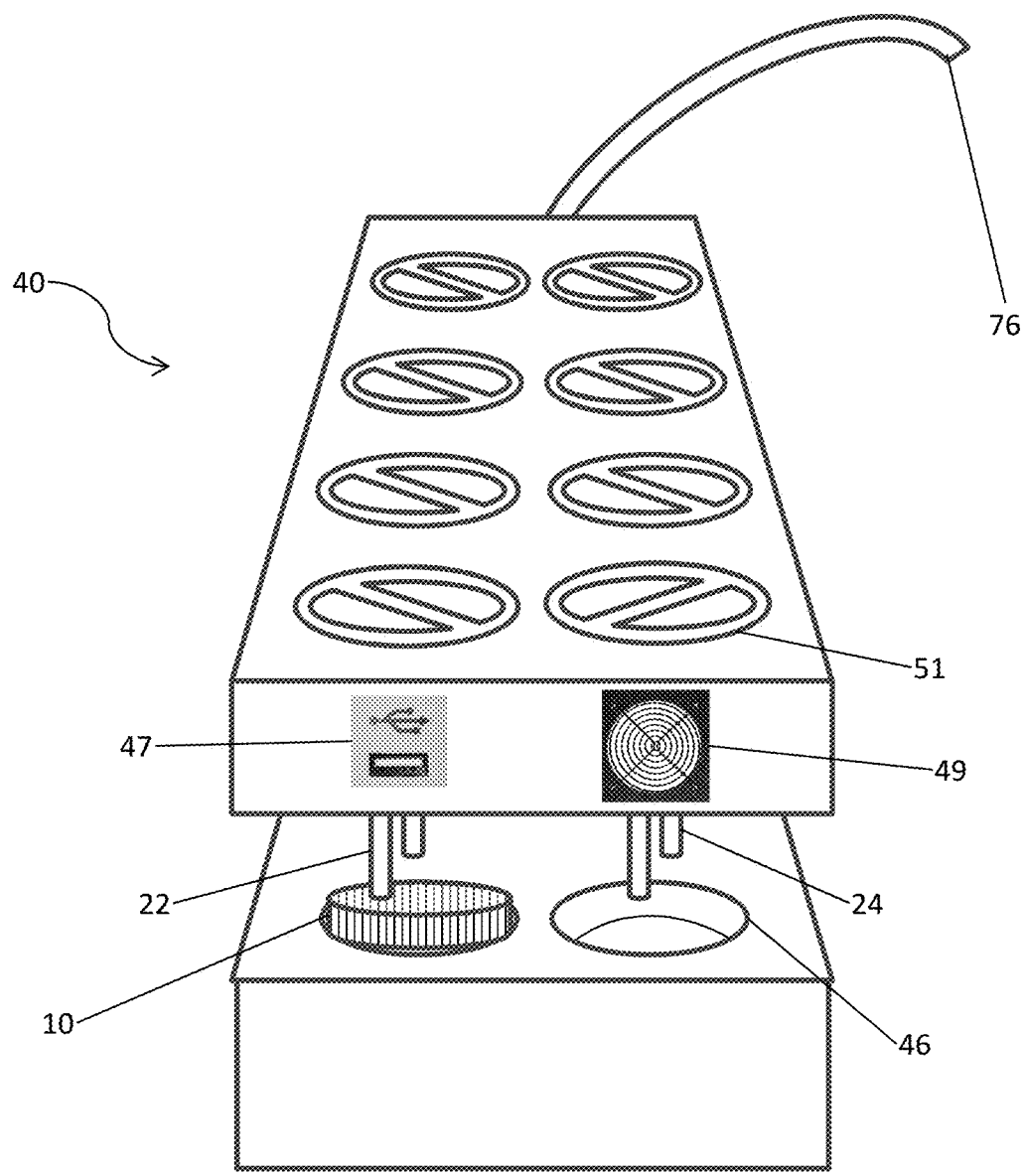
FIG. 3 illustrates a MODULE according to the present invention.

The present invention includes a module, generally described as 40 in FIG. 3, designed, constructed and configured for accepting at least one cartridge containing an odorant or selection or group of odorants to be used for testing human olfactory systems.

Preferably, the olfactometry module includes an adaptor designed, constructed and configured for accepting and activating a puncture-activated, non-resealable cartridge with an odorant, an identifier and a headspace, the cartridge standardized to provide a predetermined number of tests at a predetermined concentration into the olfactometer, a detector for measuring the gas-borne concentration of the odorant in the headspace of the cartridge, a reader for reading the identifier to determine information used to regulate gas flow within the cartridge, an air flow generator, and a network port for communicating with a computing device to provide testing data to a system for analyses and storage. The module preferably includes a database of test results.

The module is a portable and preferably wireless component that communicates with a mobile computing device to provide testing data to a system for analyses and storage, wherein the mobile computing device is, by way of example and not limitation, a smartphone, watch, tablet, or laptop computer. The module is preferably operable to connect to the cloud, the Internet, or another device via a network for analyses and storage. The module also preferably includes a system for analyzing and storing data if a network connection is unavailable. Preferably, the module uploads the analyzed and stored data to a database over a network upon restoration of the network connection. In another embodiment, the module includes a local copy of the database. Preferably, the local copy of the database was downloaded during the last network connection between the module and the mobile device. The module preferably includes an adaptor, wherein the adaptor accepts the at least one cartridge, thereby initiating function of the module. In a preferred embodiment, the module has receivers 46 for multiple cartridges 10, provides dials 51 that regulate the air flow through the cartridges, and provides a fan 49 for generating air flow. Although dials are provided in one embodiment, the airflow is preferably determined by PID measures of a concentration or volume of the odorant. In alternative embodiments, the dials are electronic and/or the air flow generator is manual.

The module includes an electronic network port 47 for electronic communication, such as, by way of example and not limitation, USB or dongle, or wireless, such as, by way of example and not limitation, Bluetooth or NFC.

In yet another embodiment, the module is for personal use and in electronic communication with a mobile computing device, which is in communication with a server and database. By way of example and not limitation, the personal module is a dongle. Apparatus for assessing olfactory system odor detection ability to predict cognitive impairment and health conditions such as diabetes.

Apparatus

The present invention provides an apparatus which improves upon a device described in Bodyak N and Slotnick B, 1999. Performance of Mice in an Automated Olfactometer: Odor Detection, Discrimination and Odor Memory. 24 (6): 637-645; which is incorporated herein by reference in its entirety. The present invention provides for a tester apparatus, generally shown as 60 in FIGS. 4 and 5, either stationary or portable, which is pre-configured to accept odorant cartridges 10 or modules 40. Although the term tester apparatus is used throughout this description, the terms an olfactory measurement apparatus and olfactory testing device should also be understood to refer to this device. These odorant cartridges contain an incorporated odorant that is releasable in predetermined amounts by the tester apparatus to form an odor in predetermined concentrations. Concentration-determining variables include odorant concentration, headspace volume, odorant surface area, odorant vapor pressure, ambient temperature, humidity, and air flow through the cartridge. Preferably, the tester apparatus is operable to determine ambient temperature and humidity. The tester apparatus can vary the amount of air flow through the cartridge in order to vary the amount of odorant released and thereby establish the odor detection abilities of the person being tested. Alternatively, the tester varies the amount of carrier air mixed with the odorized air or the aerosolized chemical exiting the cartridge to adjust the concentration of odorant to maintain a constant airflow to the person being tested. In another embodiment, the odor containment structure is a nasal mask.

Figure 4:
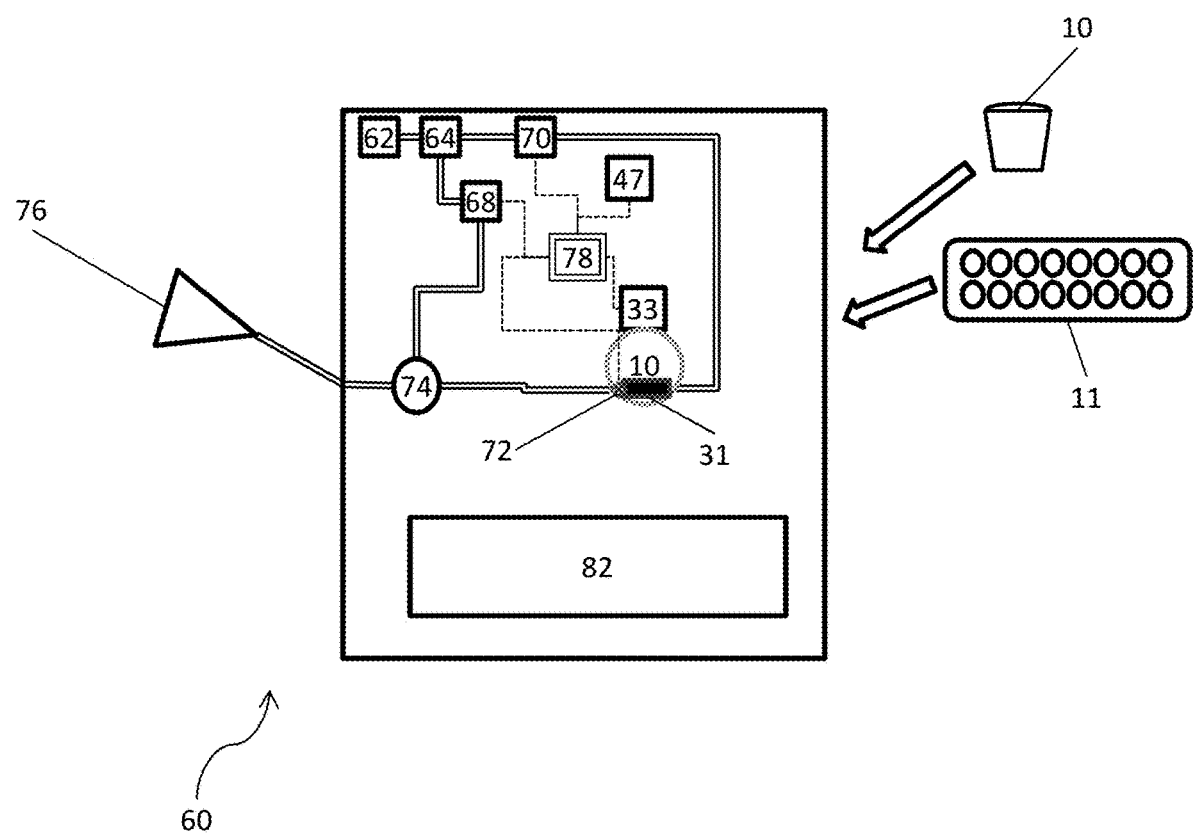
FIG. 4 illustrates an olfactory measurement apparatus according to the present invention.

As shown in FIG. 4, in a preferred embodiment the apparatus 60 includes a compressed air or gas supply 62, at least one gas filter 64, a carrier mass air controller 68, a stimulus mass air controller 70, at least one stimulus odorant container (single odorant cartridge 10 or multiple odorant cartridge 11), a detector (preferably a photo ionization detector (PID)) 72, a mixer 74, a cartridge identifier reader 33, an activator 31, an outlet 76 and a controller 78. In a preferred embodiment the compressed air is delivered to the at least one stimulus odorant cartridge 10 through stainless steel tubing, Teflon coated steel tubing, Teflon tubing, and/or glass tubing, and the air with odor is delivered to the outlet 76 through stainless steel tubing, Teflon coated steel tubing, Teflon tubing, and/or glass tubing. In a preferred embodiment, the detector 72 measures the concentration in the cartridge headspace and the odorant is heated or agitated in the cartridge until a specified odorant concentration exists in the headspace. Additionally or alternatively, the detector is incorporated into the air outlet.

An alternative apparatus is described in U.S. Provisional Patent No. 62/315,870, filed Mar. 31, 2016 and which is incorporated herein by reference in its entirety.

By way of example and not limitation, for the compressed air supply, a disposable compressed air volume (e.g., CO2 cartridge) or a small, quiet air pump is used. The apparatus is computer-controlled either directly through the controller 78 or remotely controlled via network-based communication.

Figure 5:
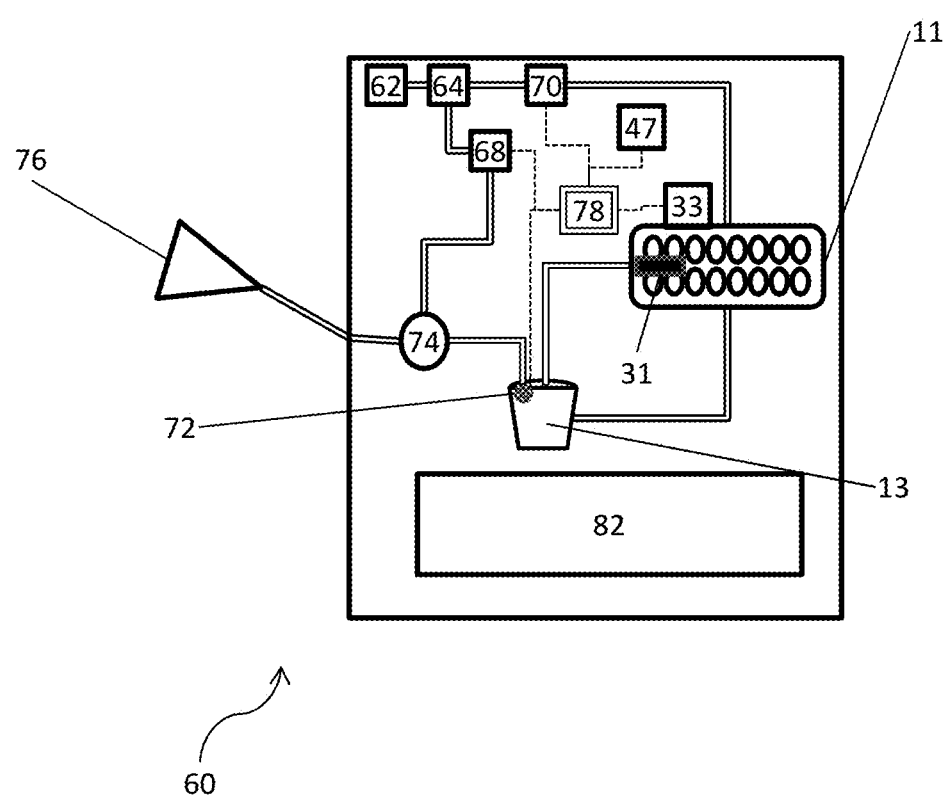
FIG. 5 illustrates another olfactory measurement apparatus according to the present invention.

In an alternative embodiment shown in FIG. 5, an extra headspace cartridge or reservoir 13 is used to provide extra headspace. Airflow through the odorant cartridge is routed to the extra headspace cartridge. When a test is actuated, the test air is taken from the extra headspace cartridge. Between tests the air is recirculated between the odorant cartridge and extra headspace cartridge to ensure the appropriate concentration of odor in the extra headspace cartridge.

The compressed air is channeled through the at least one odorant container, which is directed into the disposable or replaceable headspace reservoir 13 then mixed with an appropriate amount of more carrier air and sent to the mixer 74. As the stimulus air leaves the odorant container or extra headspace cartridge, the detector 72 determines if the required amount of odor is contained in the stimulus air. In the mixer, multiple stimuli odors are mixed and then sent to the output. Alternatively, fresh filtered air is pumped and channeled through the at least one odorant container.

The apparatus preferably includes an input device 82, such as a touchscreen, whereby the test administrator, the person being tested and/or other user input information, including demographic, medical, genetic, lifestyle information and the like.

The input device also provides for allowing the different users to share other database data, including social media databases, medical databases, genetic databases, genealogical databases, cognitive testing (e.g., Lumosity.com) databases and the like, which are uploaded to the system database.

Odorants may be sticky and adhere to the air flow channels, thus affect concentrations of tests. Sticking or fouling is prevented by a number of possible options, including use of concentric tubing arrangements where the odorant is presented from the center tube, into an airflow from larger surrounding tubes close to the point of emission into the area of detection testing. Desorption of air channels can also be provided by heating delivery tubing at high temperatures. For example, the air channels are stainless steel tubes, and are heated after a test to burn off the fouling odorant(s). Alternatively, the tubing between the cartridge and emission is designed and constructed to be easily changeable and inexpensive. Preferably, the tubing is operable to be cleaned for reuse or is disposable.

The apparatus includes detectors that can measure vapor concentration through such mechanisms as photoionization, thermal conductivity, charge detection, infrared absorption, etc. The apparatus then correspondingly alters the ratio of carrier air mixed with the cartridge effluent air, postpones a test, or alerts a test administrator so that only proper tests are performed. Preferably, the detector can detect the concentration of the odor in the air stream and vary the ratio of carrier air to sample air to achieve the desired concentration. Detectors include PID, charge detectors, other spectroscopy detectors and/or conductance detectors. Preferably, each cartridge automatically runs an initial calibration before testing begins. By way of example and not limitation, the cartridge is inserted, calibration is automatically performed, and testing is ready. Additionally, a control cartridge for calibrating an apparatus is provided.

The outlet preferably includes an odor containment structure, such as a funnel, nasal mask or sniff port for confining the odor such that it is not diluted by air currents. The person places his or her nose in the nasal mask to sense the odor. In a preferred embodiment, a photobeam is directed across the entrance of the odor containment structure, and when the person interrupts the photobeam, the tester emits the odor through an odor tube into the odor containment structure.

The present invention reduces the cost of testing humans for olfactory abilities through various ways. For example, the odorant cartridges are disposable, which allows proper standardization between cartridges and olfactometers so that the system and methods for testing are standardized. Furthermore, the testing time is decreased because the present invention increases the testing rate and reduces the preparation time, error rate and cleanup time versus prior art methods.

System for assessing olfactory system odor detection ability to predict cognitive impairment and health conditions such as diabetes, exposures to toxins, allergies, and/or idiopathic conditions and diseases.

Figure 6:
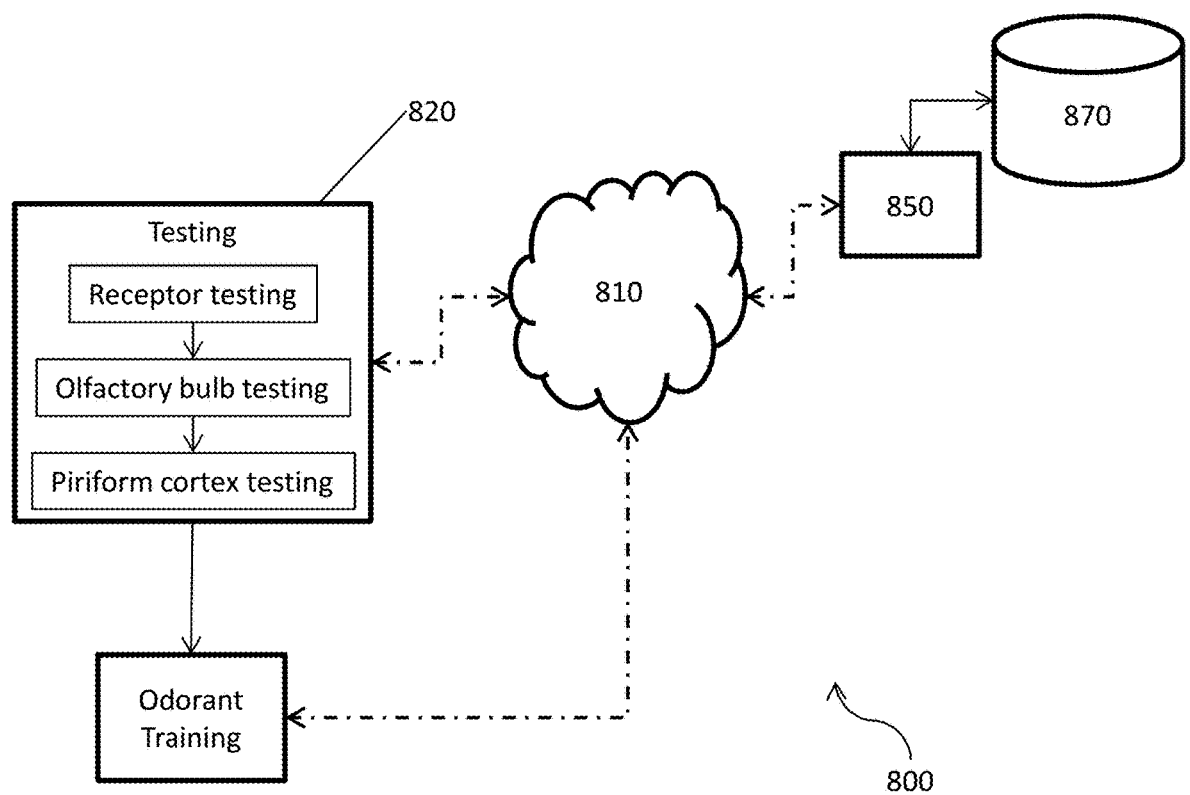
FIG. 6 illustrates a system according to the present invention.
Figure 9:
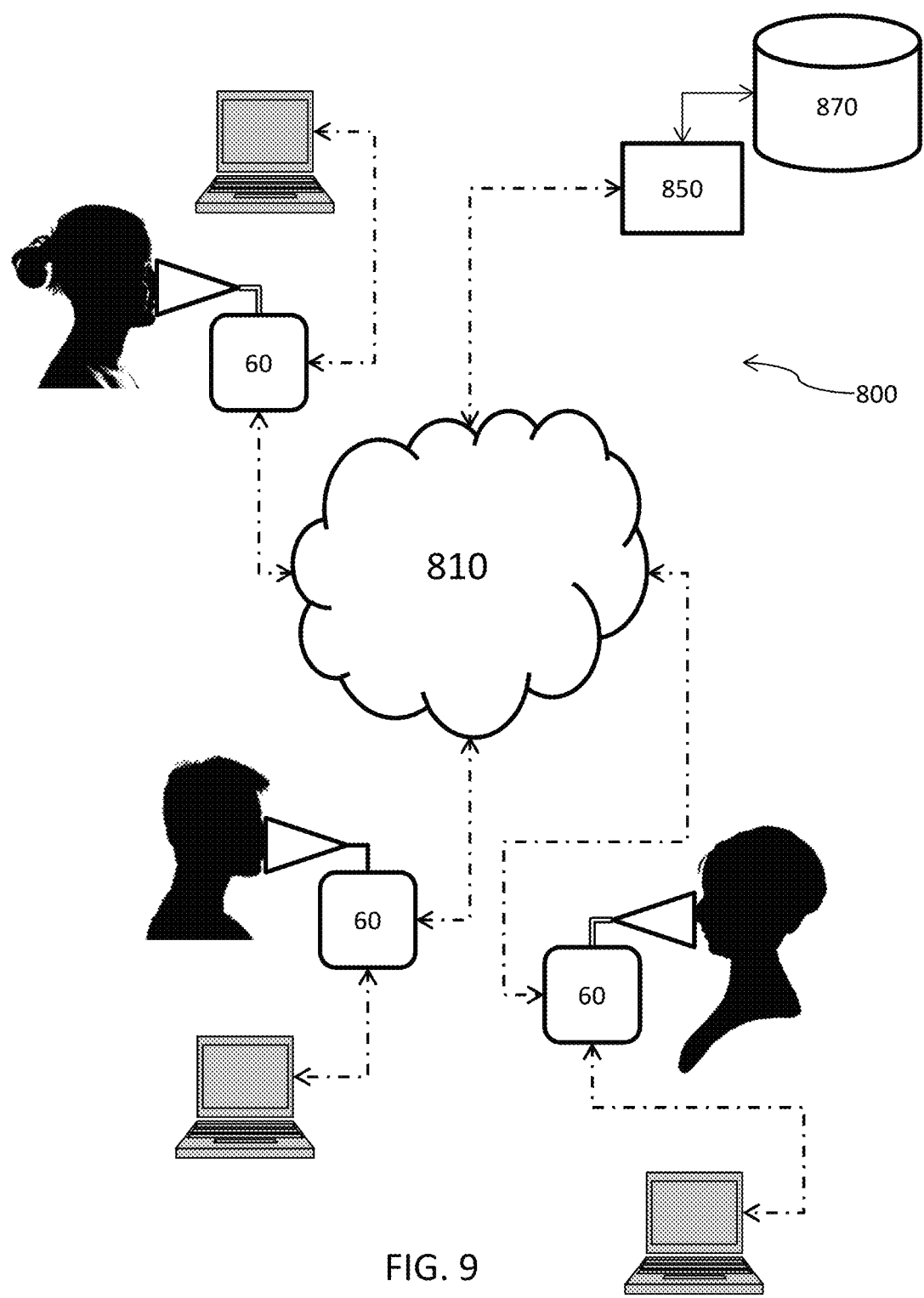
FIG. 9 illustrates another testing system according to the present invention.
Figure 10:
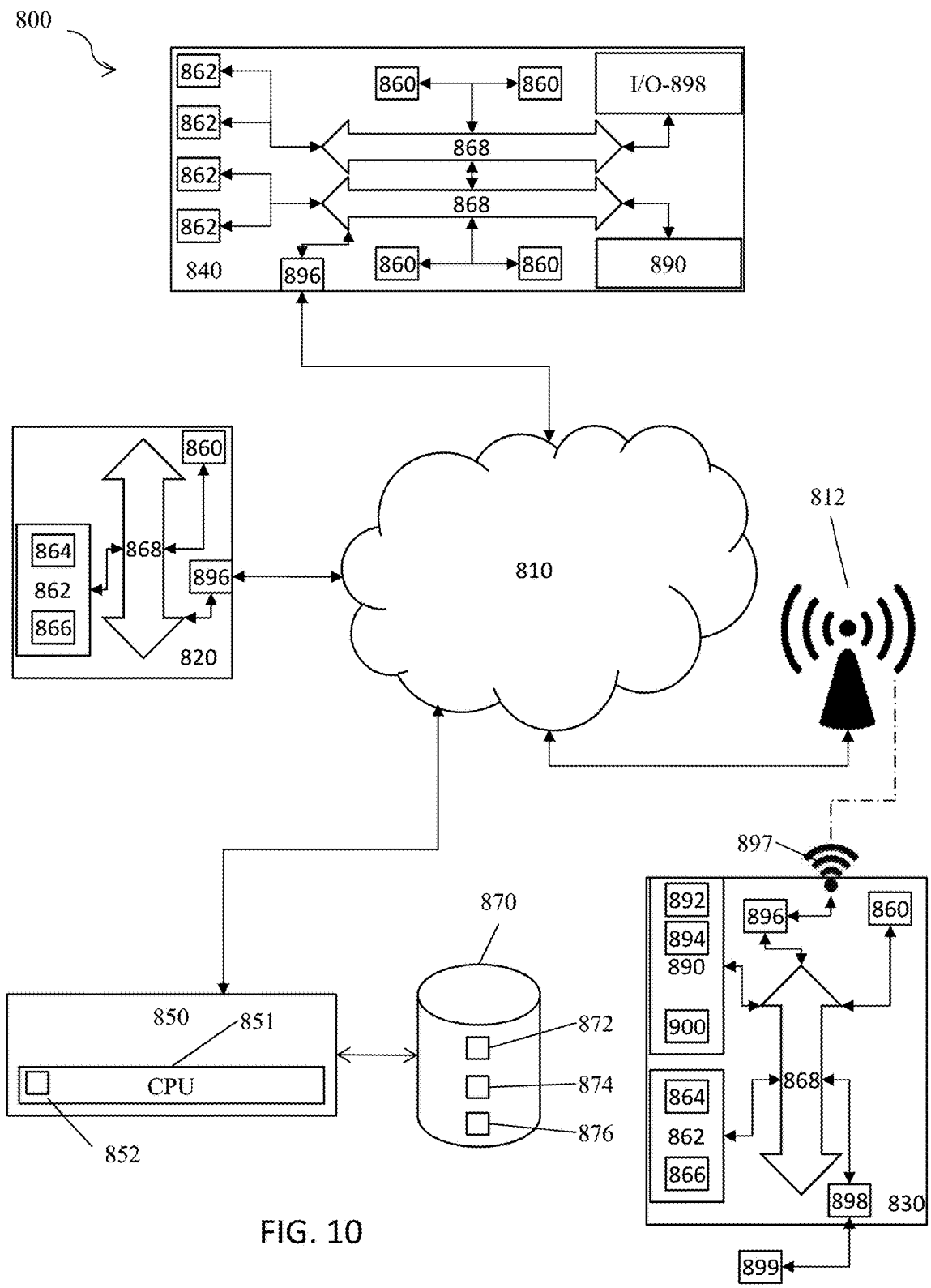
FIG. 10 is a schematic diagram of an embodiment of the invention illustrating a computer system for use with the present invention.

The present invention provides for a system, generally described as 800 in FIGS. 6, 9 and 10, for testing and validating the smelling ability of humans. The system includes at least one tester apparatus 60 in communication through a wired or wireless electronic network 810 with a server 850. In one embodiment, the tester is not necessary to the function of the system as the apparatus controls itself or testing and validating is performed remotely. The server is in communication with a population database 870 of test results. Preferably, the population database 870 of test results includes previous longitudinal olfactory measures from the same individual. The system preferably provides for several or numerous tester apparatuses to independently transmit test results to the server. The server compares received results to the previous results for that patient and/or to the population database and also updates the population database with the results. The compared results, shown in FIG. 7, are transmitted back to the tester or local computing device associated with the tester. This real-time or near-real-time analysis and reporting of data enables the rapid screening, assessment, and comparison of test subjects. Furthermore, the system transmits new programs and stimulus conditions to testers.

The present invention also provides for semi-autonomous administration of tests, wherein the apparatus is able to provide tests without connection to a server, but once the apparatus is in network communication with the server, the test data are uploaded and analysis performed at the server.

In another embodiment, the apparatus is a remote-controlled device, wherein the tests are administered from a remote location. In these embodiments, the test administrators can instruct the person being tested via GUI or voice instructions, or conduct the test automatically with the patient or subject without input from a local administrator.

Database

Figure 8:
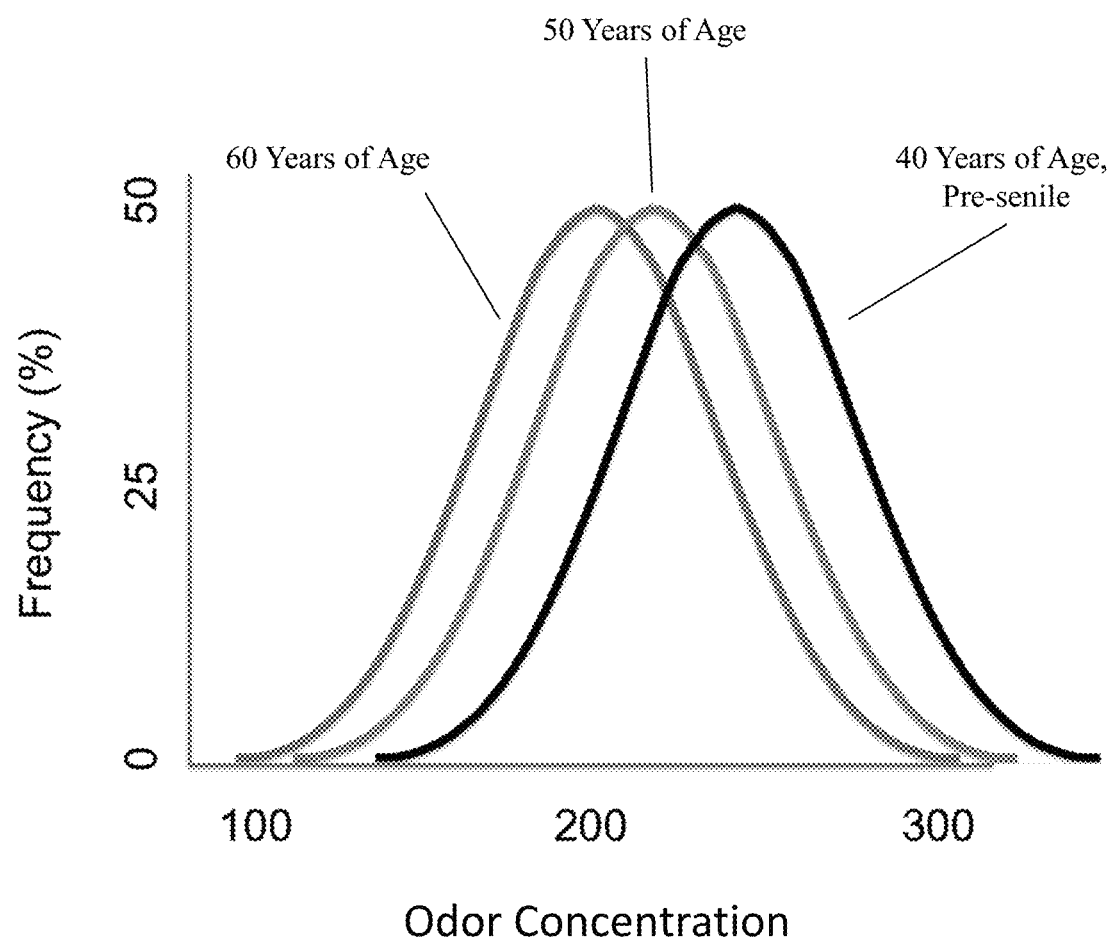
FIG. 8 illustrates an individual's longitudinal results compared to a population distribution over time.

In a preferred system, the assessments are more valid and reliable when the instant scores or results are compared against a population database of standardized test results. Preferably, the population database is a demographically appropriate database selected from an overall population database. The comparison may be limited to assessments of the individual in past tests or limited to assessments of family members of the individual in past tests. This provides for longitudinal testing. In one embodiment, the population database of test results includes demographic sub-populations, wherein the assessments of the instant scores or results are compared against one or more relevant demographic sub-populations. Preferably, the demographic sub-populations are constructed by age, weight, gender, socioeconomic status, ethnicity, height, genetic predispositions, existing health conditions, and combinations thereof. Preferably, the instant results populate and grow the database to further enhance the reliability of the population database. Preferably, the instant results are validated or verified prior to being incorporated in the database. The database contains population distributions, such as shown in FIG. 8, for a variety of odorants, such as, by way of example and not limitation, pure compounds, compound mixtures, masking compounds and masking mixtures. Preferably, common odorants such as rose, clove, eucalyptus, and lemon are used for odor identification, with pure odorants being used for sensitivity. For example, a population distribution exists for methanol, butanol, or methanol and butanol mixed. Significantly, the device of the present invention affords standardized quantifiable data so assessment verification can be performed.

Preferably, the population database only includes dynamic, collected population data. The dynamic, real-time updating of the database provides for testing against the most current data. Furthermore, changes in populations can also be tracked over time with the present invention. Thus, not only can individuals be compared to populations, but cohort populations can also be compared to previous populations to see if the population is varying.

Alternatively, test comparisons are initially performed using variances or estimated standards. A database for the new population is simultaneously populated with data collected via testing until a given number of records populate the database, at which point the comparisons are performed against the database of collected population data.

Also alternatively, the testing is started without standards and the comparisons are performed after a sufficient number of persons are tested to create a population variance.

A population database according to the present invention includes, by way of example and not limitation, demographic, medical, and occupational variables of humans. Demographic variables include race, age, marital status, occupation, income, religion, residence, ethnicity, diet and sex. Medical variables include existing co-morbidities, family history, medications and genetics. Occupational variables include sport and chemical exposure. Other database that can be used include genetic databases, genealogical databases, and cognitive testing (Lumosity.com) databases.

Another database embodiment provides for a database that contains population distributions for any olfactory test with any pure compound or compound mixture based on where in the olfactory system anatomy they are tested: the receptor, olfactory bulb, or piriform cortex, and/or prefrontal cortex. In general, the present invention provides for addressing disease processes and injury at different locations in the olfactory nervous system pathway, for example, but not limited to in odor detection in the olfactory epithelium (with olfactory sensory neurons), odor discrimination in the olfactory bulb, odor identification in the piriform cortex and odor adaptation in the epithelium.

For example, a pure monomolecular chemical, such as methanol, has a population distribution for detection, threshold testing, and/or overall sensitivity testing at the receptor, whereas a mixed compound, such as methanol and butanol, has a population distribution for testing and discrimination at the olfactory bulb.

Odorants include complex odorants that include more than one odorant, such as, by way of example and not limitation, natural odorants such as coffee, grass, gas, and the like.

Another embodiment provides for a database that contains population distributions developed from odorant testing of a compound specific to an odor sensing nerve type, wherein the compound is pure, mixed, or masking and the nerve type is olfactory (CN1) or trigeminal (CN5).

Another embodiment provides for a database that contains population distributions developed from odorant adaptation, wherein the distribution is time-to-adaptation for specific pure or mixed compound(s).

In a preferred embodiment, the population distributions within a population database are normalized. By way of example and not limitation, a normal distribution is z-score normalized. This normalization allows test scores to be compared against the variance of the population, thereby confirming where in the population the person lies. In another embodiment, the population database is a population of absolute and relative concentration values. In yet another embodiment, a separate population database exists for absolute and normalized populations.

Computing System

FIG. 10 is a schematic diagram of an embodiment of the invention illustrating a computer system, generally described as 800, having a network 810, a plurality of computing devices 820, 830, 840, a server 850 and a database 870.

The server 850 is constructed, configured and coupled to enable communication over a network 810 with a computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by a plurality of mobile communication computing devices 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, a personal digital assistant (PDA), a smart phone, a desktop computer, a netbook computer, a tablet computer, a workstation, a laptop, and other similar computing devices. The components shown here, their connections and relationships, and their functions, are meant to be exemplary only, and are not meant to limit implementations of the invention described and/or claimed in this document.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 10, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, disks or discs (e.g., digital versatile disks (DVD), HD-DVD, BLU-RAY, compact disc (CD), CD-ROM, floppy disc) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 10, may include other components that are not explicitly shown in FIG. 10, or may utilize an architecture completely different than that shown in FIG. 10. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

By way of definition and description supporting the claimed subject matter, preferably, the present invention includes communication methodologies for transmitting data, data packets, messages or messaging via a communication layer. Wireless communications over a network are preferred. Correspondingly, and consistent with the communication methodologies for transmitting data or messaging according to the present invention, as used throughout this specification, figures and claims, wireless communication is provided by any reasonable protocol or approach, by way of example and not limitation, Bluetooth, Wi-Fi, cellular, zigbee, near field communication, and the like; the term "ZigBee" refers to any wireless communication protocol adopted by the Institute of Electronics & Electrical Engineers (IEEE) according to standard 802.15.4 or any successor standard(s), the term "Wi-Fi" refers to any communication protocol adopted by the IEEE under standard 802.11 or any successor standard(s), the term "WiMax" refers to any communication protocol adopted by the IEEE under standard 802.16 or any successor standard(s), and the term "Bluetooth" refers to any short-range communication protocol implementing IEEE standard 802.15.1 or any successor standard(s). Additionally or alternatively to WiMax, other communications protocols may be used, including but not limited to a "1G" wireless protocol such as analog wireless transmission, first generation standards based (IEEE, ITU or other recognized world communications standard), a "2G" standards based protocol such as "EDGE or CDMA 2000 also known as 1xRTT", a 3G based standard such as "High Speed Packet Access (HSPA) or Evolution for Data Only (EVDO), any accepted 4G standard such as "IEEE, ITU standards that include WiMax, Long Term Evolution "LTE" and its derivative standards, any Ethernet solution wireless or wired, or any proprietary wireless or power line carrier standards that communicate to a client device or any controllable device that sends and receives an IP based message. The term "High Speed Packet Data Access (HSPA)" refers to any communication protocol adopted by the International Telecommunication Union (ITU) or another mobile telecommunications standards body referring to the evolution of the Global System for Mobile Communications (GSM) standard beyond its third generation Universal Mobile Telecommunications System (UMTS) protocols. The term "Long Term Evolution (LTE)" refers to any communication protocol adopted by the ITU or another mobile telecommunications standards body referring to the evolution of GSM-based networks to voice, video and data standards anticipated to be replacement protocols for HSPA. The term "Code Division Multiple Access (CDMA) Evolution Date-Optimized (EVDO) Revision A (CDMA EVDO Rev. A)" refers to the communication protocol adopted by the ITU under standard number TIA-856 Rev. A.

It will be appreciated that embodiments of the invention described herein may be comprised of one or more conventional processors and unique stored program instructions that control the one or more processors to implement, in conjunction with certain non-processor circuits, some, most, or all of the functions for the systems and methods as described herein. The non-processor circuits may include, but are not limited to, radio receivers, radio transmitters, antennas, modems, signal drivers, clock circuits, power source circuits, relays, current sensors, and user input devices. As such, these functions may be interpreted as steps of a method to distribute information and control signals between devices. Alternatively, some or all functions could be implemented by a state machine that has no stored program instructions, or in one or more application specific integrated circuits (ASICs), in which each function or some combinations of functions are implemented as custom logic. Of course, a combination of the two approaches could be used. Thus, methods and means for these functions have been described herein. Further, it is expected that one of ordinary skill in the art, notwithstanding possibly significant effort and many design choices motivated by, for example, available time, current technology, and economic considerations, when guided by the concepts and principles disclosed herein, will be readily capable of generating such software instructions, programs and integrated circuits (ICs), and appropriately arranging and functionally integrating such non-processor circuits, without undue experimentation.

Analyses

Together, these variables are analyzed to identify health conditions or to predict a person's risk of cognitive decline. An olfactory function assessment is performed and the results compared against an appropriate population database. By way of example and not limitation, a 60-year old female would be assessed on her odor detection ability of cinnamaldehyde. Her quantified ability to detect a given concentration of cinnamaldehyde would be analyzed and compared against other 60-year old females, her own threshold at a younger age, and/or a combination of other 60-year old females, the 60-year old females' threshold at a younger age, and her own threshold at a younger age. The analysis is selected from, by way of example and not limitation, discriminate, regression, or mixed model, and the comparison appears as, by way of example and not limitation, a percent rank or variance from the population mean.

In a preferred embodiment individual olfactory measures for odor detection/sensitivity, odor identification, odor discrimination, and odor adaptation are compared with longitudinal results from the same individual or from the same demographic comparison group to compute a numerical metric of function (Olfaxis Index). Thus, a variety of Olfaxis Indices are preferably utilized in the present invention: sensitivity metric (S-Olfaxis Index), odor identification metric (ID-Olfaxis Index), an individual sensitivity metric (Ind-Sensitivity Olfaxis Index), a threshold metric (T-Olfaxis Index), etc. These metrics are preferably used to determine functional status.

Preferably, the odor identification metric (ID-Olfaxis Index), or identification performance, is measured by presenting between a minimum of 6 individual odors and a maximum of 25 individual odors to the individual. Preferably, the individual is given a list of possible odors to choose from for each individual odor presented to the individual user. In one embodiment, the list is a list of 4 possible odors. In another embodiment, the individual is not given a list of possible odors to choose from. In one embodiment, a plurality of odors is mixed and the individual identifies as many of the plurality of odors in the odor mixture as possible.

In one embodiment, assessment to obtain data for calculating a sensitivity metric (S-Olfaxis Index), an individual sensitivity metric (Ind-Sensitivity Olfaxis Index), and/or a threshold metric (T-Olfaxis Index) is performed by testing an individual at a high concentration of an odorant in a carrier gas and lowering the concentration of the odorant in the carrier gas serially through repeated tests until the individual does not recognize that an odorant is present or until the individual cannot identify the odor produced by the odorant. In another embodiment, an assessment is performed by testing an individual at a low concentration of an odorant in a carrier gas and raising the concentration of the odorant in the carrier gas serially through repeated tests until the individual recognizes that an odorant is present or until the individual can identify the odor produced by the odorant. In yet another embodiment, an assessment is performed using one or more odorants at standard or predetermined concentrations and an individual is asked to identify the odor produced from the one or more odorants. Preferably, the individual is given a list of odors to choose the one or more odorants from.

A given assessment preferably reveals where a person fits on at least one cohort or otherwise related population distribution. A given set of longitudinal assessments, wherein longitudinal assessments are more than one assessment over time, reveal how the olfactory functions of a person compares to appropriate populations for a given odor over a given period of time.

In one embodiment, an Olfaxis Index is calculated by dividing data obtained from a current assessment of an individual to data obtained by a past assessment of the individual or by data obtained by past assessments of a suitable normalized population distribution. In one embodiment, the data is a minimum concentration of odorant in a carrier gas necessary to obtain a positive response from the individual. In another embodiment, the data is the number of odors correctly identified by the individual. In another embodiment, the data is a percentage of odors correctly identified by the individual. In one embodiment, the positive response is an acknowledgment of a presence of an odor. In another embodiment, the positive response is an identification of the odor present.

An individual's threshold metric is preferably calculated by giving an assessment to the individual for his or her smelling ability and comparing the assessment of the individual to one or more past assessments of the individual and/or to past assessments of a suitable demographic population. For example, an individual receives an assessment for his or her smelling ability, wherein the analysis and results reveal that individual's threshold sensitivity is four times the mean of the appropriate normalized population distribution, yielding a metric (Olfaxis Index) of 0.25. If in a set of longitudinal assessments that individual continues to score an Olfaxis Index of 0.25, or for an example 2 standard deviations below the mean, then further medical or cognitive examination may not be warranted, because the individual only has a poor odor detection ability without predicted cognitive decline. Preferably, this analysis is automated.

In another example, if individual A had odor sensitivity measured today, his performance could be compared with the same measure made 12 months ago. If the measures are the same, his sensitivity metric (S-Olfaxis Index would be 1.0). If his odor sensitivity for the same odorant was decreased, and his threshold was twice what it was 1 year ago, his sensitvity metric (S-Olfaxis Index) for the odorant would be 0.5.

In yet another example, if individual A had odor identification performance measured today, his performance could be compared with the same measure made 12 months ago. If the measures are the same, his odor identification metric (ID-Olfaxis Index would be 1.0). If his ID for same odorant was decreased, and his odor ID score was half what it was 1 year ago, his odor ID metric (ID-Olfaxis Index) for the odorant would be 0.5.

In another example, if the individual has undergone a single olfactory test, the results are preferably compared against the database for appropriate demographic population. If the individual's thresholds are three times higher than the comparison demographic threshold, the metric (Ind-Sensitivity Olfaxis Index) will be 0.333.

In another example, an individual's threshold for two odorants might be quantitatively compared to compute an objective metric of function. In this embodiment, an odorant that activates the trigeminal nerve (ex: carbon dioxide) might be used as a standard, against which changes in olfactory nerve function (ex: for vanillin odorant) might be quantified (T-Olfaxis Index).

In another embodiment, an individual's performance on different olfactory tests constructed to measure olfactory performance at different levels within the olfactory central nervous system might be compared to identify the pathological brain region. Odor thresholds may reflect the functional status of olfactory receptors in the olfactory epithelium. Olfactory discrimination measures may reflect functional condition of the olfactory bulb. Odor adaptation measures function of the olfactory receptor in the epithelium and in the piriform cortex. Olfactory identification measures may reflect functional condition of the piriform cortex or prefrontal cortex.

Comparison of each of these measures with comparable measures from the appropriate demographic population would generate a metric indicating the level in the central nervous system affected by mental/physical health problems or neurological disorder. For example, if odor threshold was normal (Olfaxis Index of 1.0), and odor discrimination had an Olfaxis Index of 1.0, but Odor ID had an Olfaxis Index of 0.2, then the individual might be referred for MRI and cognitive testing.

A decline in odor detection ability is known to accompany physiological ageing, senility, and other health conditions. Therefore, a set of population distributions within the population database would reveal a hyposmic shift with age of a specific population, such as male, away from a normal or pre-senile population. This hyposmic shift would happen at a mean rate over a given set of years: The hyposmic shift in 10-year increments reveals ageing population progression below the normal, pre-senile population mean as shown in FIG. 8, for example, at 40, 50, and 60 years of age. This rate of physiological decline is preferably assessed for a number of odorants.

However, if in an example set of longitudinal assessments that same individual progressively scores 0.8, 1.0, 1.2, and 1.5 standard deviations below the mean for a cohort or otherwise appropriate population, then further cognitive examination or health evaluation may be warranted, since declining odor detection ability relative to an appropriate population is strongly correlated with cognitive decline. Evaluating how an individual person's odor detection ability changes over time relative to the population is more important for the purposes of predicting cognitive decline than how that individual compares to a given population at a given time.

Figure 7A:
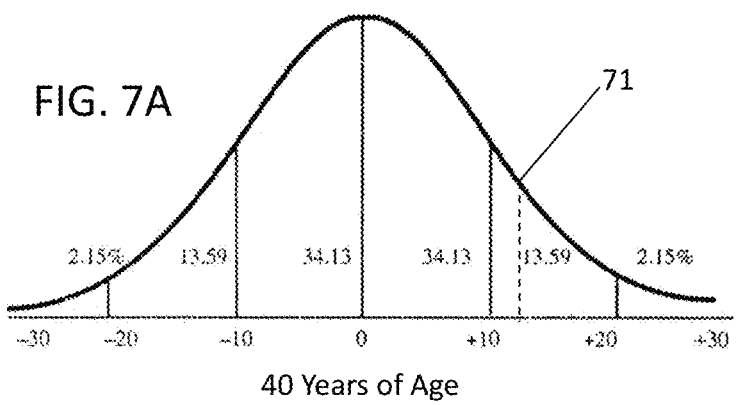
FIG. 7A-C illustrates population distributions of normal cognitive decline associated with ageing.
Figure 7B:
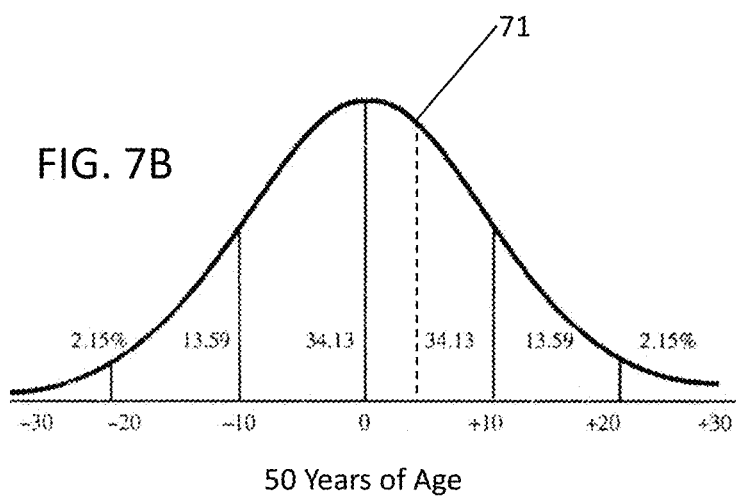
Figure 7C:
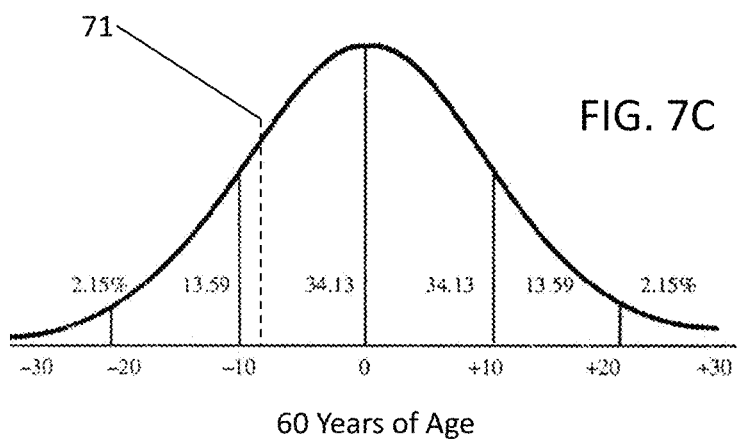

A comparison against the physiological ageing decline in odor detection of a given odor or mixture of odors is thus used to detect a decline in pathological odor detection. For example, as shown in FIG. 7A-C, if the individual's results 71 shift hyposmically at a faster rate than that of physiological ageing (independent of initial assessment), then a preliminary diagnosis of cognitive decline is made.

Analysis of the combined population database and the medical history of the testers provides for the identification of predictive or pathognomonic odor losses or patterns of odor losses. These odors can then be used in early-screening tests to reverse, prevent, or slow down disease progression.

Reaction time (RT) can also be used as an indicator of stimulus salience. For example, if the concentration is very high and therefore very obvious or salient to the animal/person, the reaction time is very brief. If the concentration is very low and near threshold, the reaction time is relatively long. Therefore, the detector is designed, configured, and constructed to measure the reaction time of the test subject.

Olfactory Pathway Analysis

A preferred use of the present system is determining where in the olfactory system pathway a decline in odor detection, adaptation, discrimination and/or identification exists. The olfactory system pathway consists of receptors at the epithelium in the nose, the olfactory bulb, the piriform cortex, and the prefrontal cortex. The receptors detect when an odor is present. The olfactory bulb discriminates between odors and whether the odor stems from a pure or mixed odor. The piriform cortex and prefrontal cortices identify (or name) the odorant associated with the pure or mixed odor. Odor adaptation occurs both in the olfactory receptors and in the piriform cortex. Identifying which link in the olfactory system pathway declines preceding cognitive decline has been difficult. Resolving this difficulty is possible with a method of the present invention. Population distributions are generated for at least one odor at each link in the olfactory system using the different olfactory measures (detection, discrimination, adaptation and odor identification). Next, an individual is tested with a pure or mixed odor to target each link in the olfactory system. The test results are then compared to an appropriate population to compute a level metric (Olfaxis Index). Thus, when an assessment is performed, analyzed, and compared to a population distribution, the metric results indicate where in the olfactory central nervous system decline exists. The assessment is also compared longitudinally with a subject's own data in one embodiment. This early and precise detection, along with medical history and demographic information, enables earlier diagnosis and more efficacious therapy to prevent, reverse, or slow the rate of cognitive decline or other health conditions such as diabetes.

A preferred test using the present system is for testing odor detection sensitivity, wherein the odor concentration is serially increased or decreased to identify a person's limit of detection for the specific odorant used. The individual's test data for the specific odorant are compared against the specific odorant's population distribution within the appropriate population database to compute a sensitivity metric (Olfaxis Index). The comparison allows discrimination of smelling ability between persons. Further, a concentration threshold for a specific odorant or mixture of odorants is then generated for the individual.

Further, testing qualifies a person's smelling ability by stratifying concentration thresholds into categories, such as, by way of example and not limitation, very poor, poor, average, good, and very good. The categories may also include the Olfaxis Index of the present invention. Preferably, the sensitivity metric (Olfaxis Index) is determined using a ratio of threshold for an olfactory odor (which would change with age and pathology) to a trigeminal odorant (which may or may not change). The trigeminal odorant is operable to serve as an in person control against which the changed olfactory odorant could be compared.

The database and analyses of the present invention can support pharmaceutical clinical trials. A pharmaceutical's efficacy is measured by a person's improvement in smelling ability.

Kiosk

The present invention can also be provided as a kiosk in such places as health clubs, medical offices and any other location that could benefit from self-testing of olfactory abilities by many persons. The kiosks are preferably pre-programmed with testing protocols and provide test results that are uploaded anonymously to the population database.

Applications

Numerous applications exist for the systems and methods of the present invention. Most prominent is the area of cognitive assessment, as previously discussed. Other applications include gaming, market research and occupational screening and training.

Games

Various possible types of games exist that utilize the present invention, including odor puzzles, odor rankings, and odor memory.

Create a Recipe—A game that combines odor puzzles with odor rankings is a game to create a recipe (complex odorant). The game includes the following steps: a player is given at least one odor; the player adds complementary odors, then shares the "recipe" with a social network without revealing the components. Social networkers smell the blend of odors, try to guess the components and rate the "recipe". Data are uploaded into an ad hoc database and each social networker then is compared to the ad hoc population database.

Mix—In this game the components of a complex odorant are added sequentially until the player can identify the complex odorant.

Unmix—In this game a masked common odorant is provided. Players attempt to guess the common odorant as they remove masking odors. Masking odors are removed until they can identify the common odorant.

Market Research

While market research for consumer preferences is known in the art, the systems and methods of the present invention enable and facilitate this research. Various types of information are obtained, especially the detection, discrimination, identification and adaptation abilities for individual odors sorted by demographics, such as ethnicity and age.

"What Does It Need?"—This is a game that combines market research with social network gaming. Market researchers provide a base recipe with at least one missing ingredient to a social network. Players attempt to find the best ingredient(s) to add. Responses are uploaded to an ad hoc database, rated by the social network, and individual rankings reported back to the players. The results are used by the market researchers to formulate new products.

Odor Detection Assessment and Training

The system of the present invention is used to train an individual's ability to detect specific odors, as shown in FIG. 6. In one embodiment, specific odors include those that are critical to safety. By way of example and not limitation, an individual is trained to detect thiols, so that he or she is able to detect a natural gas leak. Other critical odors include those associated with food spoilage, such as yeast, mold, or bacteria-mediated odors. Thus, the present invention is used to ensure that elderly persons are safe to be left alone. Additionally or alternatively, by way of example and not limitation, applications of the odor detection assessment systems and methods of the present invention are useful for application by insurers to screen applicants for health coverage; by employers to verify training, by military to track effects of training and/or combat, and/or to determine if an elderly or disabled person is safe left alone (able to detect spoilage, gas, smoke, etc.).

Numerous occupations require that persons be able to detect low levels of certain odors, or, conversely, not smell low levels of certain odors. For example, many biological processes have highly variable starting ingredients and therefore require that the worker be able to sense when a process is complete. In the context of wine, detecting presence of one odorant in a complex, or one volatile in the wine, is a skill useful or even required for sommeliers. The ability to smell the completion of a process can thus be important. Therefore, the need exists for workers to be screened and/or trained for their detection level of certain odors, as well as their ability to discriminate and identify the odors when in a complex mixture or masked. An example application is coffee bean roasting. Because of the variability in bean content, the roasting process to achieve optimum aroma and reduce undesirable odors due to charring is variable, and therefore the roaster needs to be able to 1) detect and identify at very low concentrations the odors that signal the onset of charring and 2) adapt to roasting odors in order to detect the completion of roasting. The ability to quickly and inexpensively screen and further train these workers satisfies this long-standing, unmet need and results in better coffee.

Method for Assessing Olfactory System Odor Detection Ability to Predict Cognitive Impairment.

The present invention is also directed to a method for assessing olfactory system odor detection ability to predict the onset of, or be used in conjunction with other medical testing to diagnose cognitive impairment, diabetes, traumatic brain injury, ALS, Parkinson's, Alzheimer's, general non-neurodegenerative diseases, general ailments, and the like. The method of the present invention provides for assessing the odor detection, discrimination and identification ability of a human, wherein the results of the assessment are analyzed against an appropriate population database, including demographic databases, medical history databases and the like. Preferably, the results are also added to the appropriate database. The database contains at least one population distribution, wherein a distribution describes a human population's ability to detect, discriminate between, and/or identify odors.

The data delivered to a system computing device for analyses and storage is preferably first anonymized. The anonymized data, preferably edited to conform to HIPAA regulations, are aggregated to provide population distributions.

Figure 11:
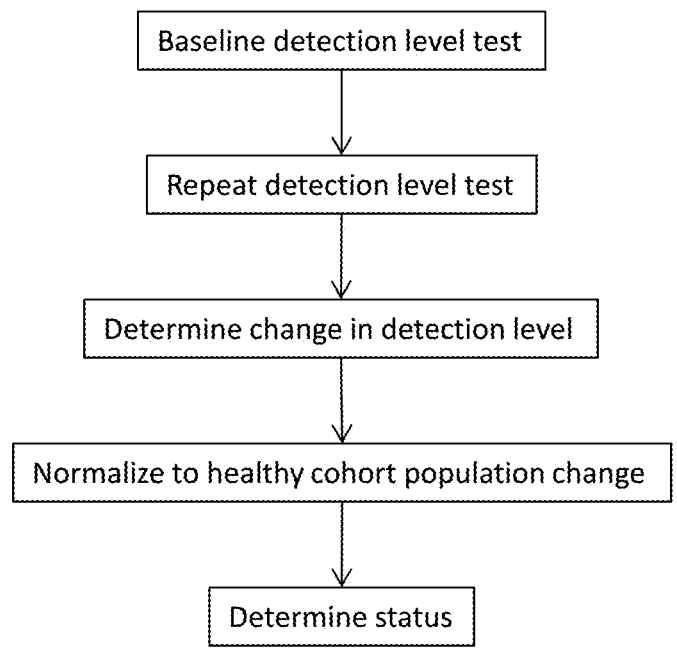
FIG. 11 illustrates a basic method for assessing cognitive decline.

FIG. 11 shows a flow diagram illustrating an example method according to the present invention. This method, which is for determining the degradation of olfactory performance over time, starts by determining the baseline detection level of a person, then determining the detection level over time. The changes in detection level are normalized to a healthy cohort population change to determine the performance status of the tested person.

The above-mentioned examples are provided to serve the purpose of clarifying the aspects of the invention and it will be apparent to one skilled in the art that they do not serve to limit the scope of the invention. By way of example, the system can identify areas needing critical odor training using analytics and/or rules engines. Further, by way of example and not limitation, the cartridge is provided with at least one microprocessor having a memory for programming for command and control of the settings of the olfactometer device based upon the particular odorant(s) within the cartridge, so that the olfactometer device automatically provides the correct airflow, etc. for the selective actuation of the predetermined odorant(s) within the cartridge. All modifications and improvements have been deleted herein for the sake of conciseness and readability but are properly within the scope of the present invention.

What is claimed is:

1. A method for testing olfactory system function, comprising:
    providing a device constructed and configured with at least one cartridge having a plurality of odorants that are selectively and controllably flowably deliverable from the device to a test subject in controlled concentrations;
    electronically determining ambient temperature and humidity and controlling the device to release odorant in the controlled concentrations;
    delivering a first odorant of the plurality of odorants from the device to the test subject at a first concentration;
    delivering a second concentration of the first odorant from the device to the test subject, wherein the second concentration is greater than or less than the first concentration; and
    determining an odor detection sensitivity threshold metric of the test subject based on a detection of the first odorant by the test subject at the first or second concentration for testing olfactory system function.

2. The method of claim 1, further comprising detecting vapor concentration of the first odorant before or during or before and during the delivering steps using a detector in a flow path in the device to measure and/or verify concentration of the first odorant is at the first concentration at its delivery and at the second concentration at its delivery.

3. The method of claim 1, further comprising:
    delivering at least a second and a third odorant of the plurality of odorants from the device to the test subject in controlled concentrations; and
    defining an odor identification metric of the test subject based on whether the test subject is able to identify the second and third odorants.

4. The method of claim 1, further comprising:
    testing for odor identification, and/or an odor discrimination, an odor adaptation, and an odor masking of the test subject using the plurality of odorants that are selectively and controllably flowably deliverable from the device to the test subject in controlled concentrations;
    generating metrics of at least odor discrimination and identification based on the testing; and
    providing an olfactory index based on the generated metrics test subject's response to the testing.

5. The method of claim 1, wherein a respective cartridge of the at least one cartridge is configured to controllably flowably introduce the first odorant into a carrier gas in a flow path in the device to provide a first odorant and carrier gas mixture, wherein the delivering steps comprises serially outputting the first odorant in the first odorant and carrier gas mixture at the first concentration, then at the second concentration.

6. The method of claim 1, further comprising:
    generating individual olfactory metrics for odor detection/sensitivity, odor identification, and odor discrimination based on test data obtained using the device to thereby evaluate different levels of the CNS;
    calculating an olfactory index by combining the generated individual olfactory metrics; and
    reporting test results comprising the olfactory index for the test subject.

7. The method of claim 1, further including the step of reporting test results of olfactory system function for the test subject compared to a population.

8. The method of claim 1, further comprising:
    determining a present minimum concentration of the delivered first odorant to obtain a present positive response from the test subject to the first odorant;
    comparing a past minimum concentration of the delivered first odorant to obtain a past positive response of the test subject to the present minimum concentration of the first odorant to obtain the positive response to the first odorant; and
    identifying whether there is a difference in sensitivity between the past and present minimum concentrations to thereby identify a possible impairment or decline in olfactory system function.

9. The method of claim 1, wherein the at least one cartridge includes an identifier with information and the device includes an identifier reader, and wherein the device uses the identifier information to control the testing including selecting an odorant from the plurality of odorants for delivery and controlling concentrations of the selected odorant for delivery.

10. The method of claim 1, further comprising:
    controlling a test protocol of the device using information comprising a plurality of: name of a target odorant of the plurality of odorants for present delivery, concentration of the target odorant in a carrier gas, headspace of the cartridge, maximum flow rate through the at least one cartridge, total actuatable volume, maximum total odorant available of the target odorant, vapor pressure, vapor ionization voltage, time required to saturate the headspace, and combinations thereof.

11. A system for testing olfactory system function, comprising:
    a compressed gas source, a carrier mass gas controller, a stimulus mass gas controller, at least one stimulus odorant cartridge including at least one odorant, at least one stimulus odorant cartridge activator, and an output;
    wherein the compressed gas source produces compressed gas to be channeled through the at least one stimulus odorant cartridge to the output; and
    wherein the carrier mass gas controller and stimulus mass gas controller control the carrier gas mass flow and the stimulus gas mass flow, respectively, to provide a controlled concentration of the at least one odorant in an odorant and gas mixture to a test subject.

12. The system of claim 11, wherein the system delivers a series of controlled concentration doses of the at least one odorant, and wherein the system comprises a detector in fluid communication with a flow delivery path upstream of the output and adjacent a headspace of the at least one stimulus odorant cartridge which provides data which the system uses to measure and/or calibrate a concentration of a respective odorant for confirming and/or providing the concentration.

13. The system of claim 11, wherein the at least one stimulus odorant cartridge is releasably held in a housing adjacent the compressed gas source that is also held in the housing, wherein the at least one stimulus odorant cartridge is configured to be serially interchangeable with a different at least one stimulus odorant cartridge, and wherein the system delivers a series of a multiplicity of odorants at controlled concentrations.

14. The system of claim 13, wherein the at least one stimulus odorant cartridge comprises a plurality of different odorants, that are held in fluid isolation from each other in the at least one stimulus odorant cartridge, and wherein the system delivers the different odorants in controlled concentrations in sufficient number to test at least (i) odor sensitivity and odor identification, and/or (ii) odor discrimination, odor adaptation, and odor masking.

15. The system of claim 11, wherein the at least one stimulus odorant cartridge comprises a plurality of different odorants that are held in fluid isolation from each other, wherein the at least one stimulus odorant cartridge is a puncture-activated, non-resealable cartridge that is configured to provide a number of one or more controlled concentrations of the different odorants and is configured to fit into at least one olfactory measurement apparatus that also encloses the first and second mass gas controllers.

16. The system of claim 11, further comprising at least one computing device configured to communicate over a network with at least one olfactory measurement apparatus that holds the at least one stimulus odorant cartridge, the stimulus mass controller and the carrier gas mass controller; and further including:
a remote database accessible by the at least one computing device over the network;
wherein the at least one computing device receives test results from the at least one olfactory measurement apparatus and stores them in the remote database, and wherein the at least one computing device compares the test results from the at least one olfactory measurement apparatus with prior acquired test results stored in the remote database and generates an olfactory index as a test result for olfactory function for respective test subjects with metrics for odor identification and odor threshold/sensitivity.

17. The system of claim 16, further comprising a multiplicity of olfactory measurement apparatuses in real-time communication with the at least one computing device and database.

18. The system of claim 11, wherein the at least one stimulus odorant cartridge includes an identifier with information and the system further includes an identifier reader, and wherein the system uses the identifier information to control the testing or access information to control the testing.

19. The system of claim 18, wherein the information used to control the testing comprises a plurality of: name of a target odorant for present delivery to a test subject, concentration of the target odorant in a carrier gas, headspace of the at least one stimulus odorant cartridge, maximum flow rate through the at least one stimulus odorant cartridge, total actuatable volume, maximum total odorant available of the target odorant, vapor pressure, vapor ionization voltage, time required to saturate the headspace, and combinations thereof.

* * * * *